United States Patent [19]

Lambert

[11] 4,446,719

[45] May 8, 1984

[54] ELECTROREFLECTANCE VIBRATIONAL SPECTROSCOPY

[75] Inventor: David K. Lambert, Sterling Heights, Mich.

[73] Assignee: General Motors Corporation, Detroit, Mich.

[21] Appl. No.: 400,869

[22] Filed: Jul. 22, 1982

[51] Int. Cl.³ .......................................... G01N 21/17
[52] U.S. Cl. ..................................... 73/23; 250/341
[58] Field of Search .................... 73/23; 250/341, 340, 250/358.1, 370, 371

[56] References Cited

U.S. PATENT DOCUMENTS

| | | | |
|---|---|---|---|
| 4,105,919 | 8/1978 | Bridges et al. | 250/341 |
| 4,186,355 | 1/1980 | Lo | 372/45 |
| 4,352,016 | 9/1982 | Duffy et al. | 250/358.1 |

*Primary Examiner*—Stephen A. Kreitman
*Attorney, Agent, or Firm*—Warren D. Hill

[57] ABSTRACT

To measure the concentration of molecules adsorbed on metal or insulator surfaces as well as their bonding to the surface and their mutual interaction, a vibrational spectroscopy method is proposed in which the infrared absorption is modulated using a first order Stark shift of the adsorbed molecule vibrational frequency. A sample surface in a high vacuum or at atmospheric pressure is illuminated by infrared radiation from a tunable diode laser an reflected radiation is detected by an infrared sensor. A high intensity electric field normal to the surface is amplitude modulated at a given frequency and the synchronous modulation of the reflected light is measured while varying the wavelength to obtain the spectra of vibrational absorption.

4 Claims, 1 Drawing Figure

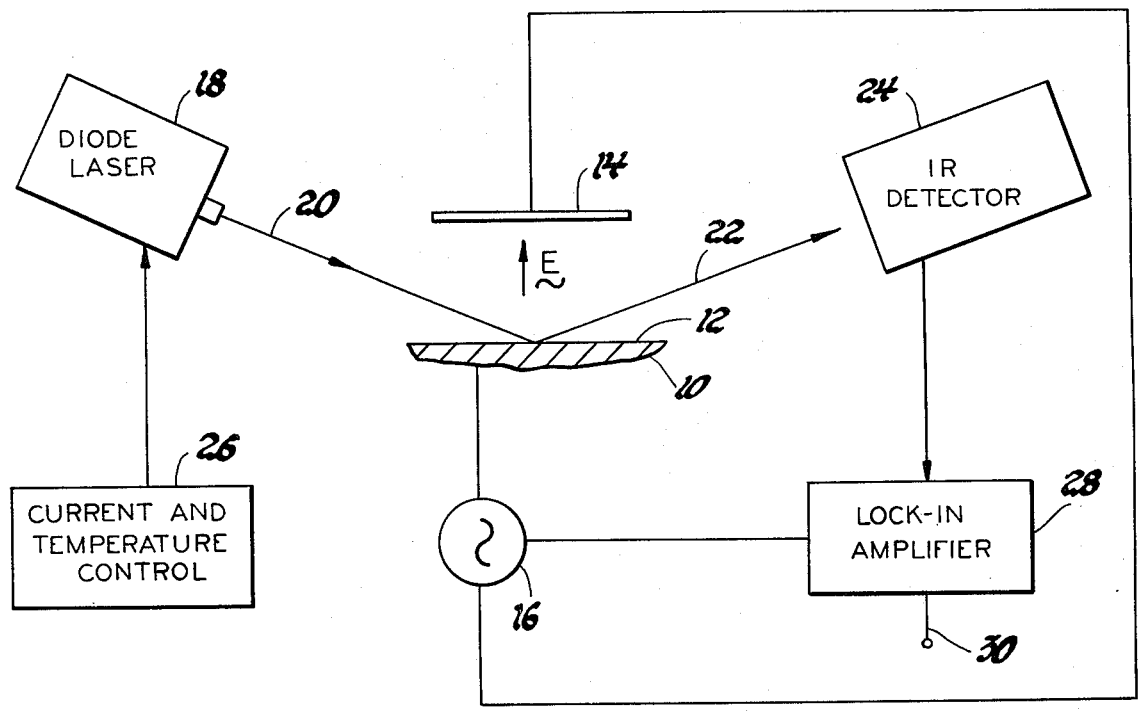

ELECTROREFLECTANCE VIBRATIONAL SPECTROSCOPY

This invention relates to infrared spectroscopy, and more particularly, to a method for electroreflectance vibrational spectroscopy.

Vibrational spectroscopy is used to measure the concentration of molecules adsorbed on surfaces. It is also used to study bonding of molecules to the surface and their mutual interaction. The need for this information in surface chemistry and catalysis studies has led to the development of many techniques to obtain it. These techniques include electron energy loss spectroscopy, infrared spectroscopy, Raman spectroscopy, several non-linear optical techniques, inelastic electron tunneling spectroscopy and neutron scattering. Each of these techniques has its own characteristics which include advantages as well as disadvantages. For example, some are useful only in conjunction with metal surfaces, some are useful only at high vacuum, others have low sensitivity.

It is a general object of this invention to provide an infrared spectroscopy method for the study of adsorbed molecules on metal or insulator surfaces which is sensitive and useful at ultra-high vacuum and at atmospheric pressure. It is a further object to provide such a method which offers resolution not afforded by other techniques.

The invention is carried out by establishing a modulated electric field at a metal or insulator surface, irradiating the surface with infrared radiation and varying the wavelength thereof, detecting the radiation reflected from the surface and measuring the synchronous modulation of reflectivity while varying the radiation wavelength to obtain the spectra of vibrational absorption.

The above and other advantages will be made more apparent from the following specification taken in conjunction with the accompanying drawing which is a diagrammatic illustration of apparatus for carrying out the method of the invention.

The drawing shows a substrate 10 of metal or an insulator having a surface 12 sufficiently flat to permit specular reflection of infrared radiation. An electrode 14 is disposed opposite the surface 12 and a high voltage AC source 16 is coupled across the substrate 10 and the electrode 14. Where the substrate 10 is metal the source 16 can be directly connected to it. However, when the substrate is an insulator then a metal backing electrode adjacent the substrate 10 is connected to the source so that an electrical field is established at the surface of the substrate. It is desirable that the electrical field intensity be as high as possible without causing an electric breakdown. This spectroscopy method is apt to be most useful at ultra-high vacuum conditions and at atmospheric pressure or higher pressures because in those circumstances high intensity electrical fields can be maintained whereas at low vacuum pressures electrical breakdown occurs at low field strengths. For pressures below $10^{-3}$ Pa field strengths between $10^4$ and $10^5$ (V/cm) can be achieved and for gas pressure of an atmosphere an electric field of the order of $10^4$ (V/cm) is obtainable. The voltage of the source 16 and the spacing between the surface 12 and electrode 14 are chosen to realize the maximum field intensity. The frequency of the source is preferred to be on the order of 20 KHz or higher.

A high intensity, low noise, tunable diode laser 18 projects a beam of infrared laser light 20 onto the surface 12 and the reflected beam 22 is measured by an infrared detector 24. The diode laser 18 is tuned through a range of wavelengths by a current and temperature control circuit 26 which is coupled to the laser. Suitable diode lasers for this application are described in the patent to Lo, U.S. Pat. No. 4,186,355, and in the article by Lo published in the AIP Conference Proceedings, Volume 66, page 72 (1981). In the case of metal surfaces any electric field component of the incident light which is parallel to the surface is not absorbed by the molecules and has no effect. Thus the polarized light 20 from the diode laser is oriented with its electric field substantially perpendicular to the surface. The angle of incidence of the light beam 20 must be a few degrees from glancing off the surface if the surface is metal. In the case of nickel, the optimum angle of incidence is about 86° from the normal to the surface.

A suitable infrared detector 24 is an Hg Cd Te photoconductor infrared detector. The detector output is fed to a lock-in amplifier 28 which has a reference input signal derived from the AC source 16. The lock-in amplifier 28 then is effective to synchronously measure the modulation of reflectivity which occurs due to the modulation of the electrical field at the surface 12 and to provide an output signal on line 30.

Molecules adsorbed on the surface 12 have a preferred orientation relative to the electric field while gas-phase molecules in equilibrium do not. As a consequence, adsorbed molecules with a nonzero dipole moment will, in general, have a first order Stark effect. The electroreflectance vibrational spectroscopy signal arises from modulation of the intensity of light reflected by the surface which is occasioned by the selective absorption of certain wavelengths by the adsorbed molecules. It can be shown that spectra of adsorbed molecules obtained with electroreflectance vibrational spectroscopy are proportional to the derivative of the spectra obtained with the conventional infrared reflection absorption spectroscopy. As a result of this derivative effect coupled with the high resolution stemming from the use of a tunable diode laser source, extremely small amounts of sharp spectral structure can be detected thus providing an outstanding advantage of electroreflectance vibrational spectroscopy over other vibrational spectroscopy techniques.

As a specific example of a procedure carried out in high vacuum to study CO adsorbed on a nickel surface, single crystal nickel is polished to provide a surface with high reflectivity to IR radiation. Then the specimen is subjected to a high vacuum and heated to de-gas the surface. The surface is then exposed to a known amount of CO for a known time to adsorb the predetermined concentration of CO onto the specimen surface. As thus far described, this procedure is well-known for the preparation of vibrational spectroscopy samples. The ultra-high vacuum is again applied to the specimen and the infrared radiation is reflected from the surface and measured while the modulated electric field is applied normal to the surface as described above. During the measurements the source is tuned throughout its range to sweep the wavelength of the radiation through the range where molecular adsorption by the adsorbed gas occurs. The reflected light signal measured by the IR detector 24 is synchronously measured by the lock-in amplifier 28 at the modulation frequency of the source 16 to detect the vibrational absorption at each wavelength of the beam 20. The measuring continues as the laser wavelength scans throughout the range of molecular absorption in order to obtain an output signal on line 30 which represents the spectra of electroreflectance vibrational absorption. The derivative spectra of conventional infrared vibrational absorption is obtained from the data by normalizing out the variation of optical intensity with laser wavelength. Alternatively, the measurements can be made at a pressure of about one atmosphere of air. Still higher air pressures may be used to allow more intense electric fields.

The modulation frequency is selected to optimize the sensitivity. Diode laser intensity noise can establish a limit to the sensitivity. For the diode laser identified above, the noise decreases as modulation frequency increases. At 20 kHz and higher frequencies the noise is small. The random noise can also be reduced by using a long integration time, that is, for each data point the measurement is made over some time interval to average out the effects of noise.

It will thus be seen that the method according to this invention allows the study of gas molecules adsorbed on the surface of a metal or insulator in high vacuum or at atmospheric pressure or higher pressures by obtaining the derivative spectra of vibrational absorption which reveals extremely small amounts of sharp spectral structure.

The embodiments of the invention in which an exclusive property or privilege is claimed are defined as follows:

1. A method of obtaining the vibrational spectra of molecules adsorbed on a metal or insulator surface comprising the steps of:
   establishing an electric field normal to the surface and amplitude modulating the electric field,
   irradiating the surface with infrared radiation and varying the radiation through a range of wavelengths corresponding to the range of vibrational absorption of the adsorbed molecules,
   detecting radiation reflected from the surface, and
   measuring the synchronous modulation of reflectivity while varying the radiation wavelength to obtain the spectra of vibrational absorption.

2. A method of obtaining the vibrational spectra of molecules adsorbed on a metal or insulator surface comprising the steps of:
   establishing an electric field normal to the surface, the field having maximum intensity insufficient to cause electrical breakdown,
   irradiating the surface with infrared radiation and varying the radiation through a range of wavelengths corresponding to the range of vibrational absorption of the adsorbed molecules,
   detecting radiation reflected from the surface,
   amplitude modulating the electric field for causing synchronous modulation of the surface reflectivity, and
   measuring the synchronous modulation of reflectivity while varying the radiation wavelength to obtain the spectra of vibrational absorption.

3. A method of obtaining the vibrational spectra of molecules adsorbed on a metal or insulator surface comprising the steps of:
   establishing at the surface a gas pressure below $10^{-3}$ Pa or at substantially atmospheric pressure so that the electrical breakdown field strength of the gas is maximized,
   establishing in the gas an electric field normal to the surface having a maximum field strength insufficient to cause electrical breakdown,
   irradiating the surface with infrared radiation and varying the radiation through a range of wavelengths corresponding to the range of vibrational absorption of the adsorbed molecules,
   detecting radiation reflected from the surface,
   amplitude modulating the electric field to effect synchronous modulations of the surface reflectivity, and
   measuring the synchronous modulation of reflectivity while varying the radiation wavelength to obtain the spectra of vibrational absorption.

4. A method of obtaining the vibrational spectra of molecules adsorbed on a metal or insulator surface comprising the steps of:
   establishing an electric field normal to the surface and amplitude modulating the electric field,
   irradiating the surface with infrared radiation and varying the radiation through a range of wavelengths corresponding to the range of vibrational absorption of the adsorbed molecules wherein the radiation intensity is subject to change as wavelength changes,
   detecting radiation reflected from the surface, and
   measuring the synchronous modulation of reflectivity while varying the radiation wavelength to obtain vibrational absorption data, and adjusting the data by normalizing out the variation of radiation intensity with changing wavelength to obtain the spectra of vibrational absorption.

* * * * *